US009677975B2

(12) United States Patent
Zhang et al.

(10) Patent No.: US 9,677,975 B2
(45) Date of Patent: Jun. 13, 2017

(54) SYSTEMS AND METHODS FOR ASEPTIC SAMPLING

(71) Applicant: General Electric Company, Schenectady, NY (US)

(72) Inventors: Chengkun Zhang, Rexford, NY (US); Kenneth Roger Conway, Clifton Park, NY (US); Donald Joseph Buckley, Schenectady, NY (US); Eugene Pauling Boden, Scotia, NY (US); Weston Blaine Griffin, Niskayuna, NY (US); Anshika Bajaj, Niskayuna, NY (US); Reginald Donovan Smith, Schenectady, NY (US)

(73) Assignee: General Electric Company, Niskayuna, NY (US)

(*) Notice: Subject to any disclaimer, the term of this patent is extended or adjusted under 35 U.S.C. 154(b) by 210 days.

(21) Appl. No.: 14/529,203

(22) Filed: Oct. 31, 2014

(65) Prior Publication Data

US 2016/0122798 A1 May 5, 2016

(51) Int. Cl.
| | | |
|---|---|---|
| *G01N 1/18* | (2006.01) | |
| *C12M 1/00* | (2006.01) | |
| *C12M 1/32* | (2006.01) | |
| *C12M 1/26* | (2006.01) | |
| *C12M 1/12* | (2006.01) | |
| *C12M 1/34* | (2006.01) | |

(52) U.S. Cl.
CPC ............... *G01N 1/18* (2013.01); *C12M 23/00* (2013.01); *C12M 23/40* (2013.01); *C12M 33/00* (2013.01); *C12M 33/06* (2013.01); *C12M 37/02* (2013.01); *C12M 41/00* (2013.01)

(58) Field of Classification Search
CPC .......... G01N 1/18; C12M 33/06; C12M 23/40
See application file for complete search history.

(56) References Cited

U.S. PATENT DOCUMENTS

| | | | |
|---|---|---|---|
| 4,999,307 | A | 3/1991 | Oakley |
| 7,052,603 | B2 | 5/2006 | Schick |
| 7,578,205 | B2 | 8/2009 | Belongia |
| 7,892,774 | B2 | 2/2011 | Rutanen |
| 7,921,740 | B2 | 4/2011 | Furey et al. |
| 8,281,672 | B2 * | 10/2012 | Lee .................. C12M 37/02 73/863 |

(Continued)

*Primary Examiner* — Justin Olamit
(74) *Attorney, Agent, or Firm* — Pabitra K. Chakrabarti

(57) ABSTRACT

A sampling assembly configured to be coupled to a sample source and facilitate aseptic sampling at one or more instances in time is provided. Further, the sampling assembly includes a first conduit having first and second ports, where the first port is configured to be coupled to the sample source. The sampling assembly also includes a plurality of sub-conduits having corresponding sub-ports, where each of the plurality of sub-conduits is operatively coupled to the first conduit at respective connector junctions. Also, each of the sub-ports is in fluidic communication with the first conduit. The sampling assembly also includes a plurality of sampling kits and one or more pumping devices. Further, each sampling kit is operatively coupled to a respective sub-port of a corresponding sub-conduit. Moreover, the one or more pumping devices are operatively and aseptically coupled to the second port of the first conduit.

19 Claims, 10 Drawing Sheets

(56) References Cited

U.S. PATENT DOCUMENTS

| | | |
|---|---|---|
| 8,518,258 B2 | 8/2013 | Balschat et al. |
| 8,609,024 B2 | 12/2013 | Ronsick et al. |
| 8,815,179 B2 | 8/2014 | Hofman et al. |
| 2005/0074872 A1* | 4/2005 | Furino .................. B01L 3/0241 435/288.4 |
| 2011/0079095 A1 | 4/2011 | Bruecher |
| 2011/0201100 A1 | 8/2011 | Proulx et al. |
| 2013/0281787 A1 | 10/2013 | Avneri et al. |

* cited by examiner

SYSTEMS AND METHODS FOR ASEPTIC SAMPLING

BACKGROUND

Embodiments of the present specification relate to aseptic sampling, and more particularly to aseptic sampling at one or more instances in time.

Typically, in a cell culture process, growth media is used to nourish cells and carry away cell-secreted products. The growth media is provided continuously or intermittently to a culture vessel for in vitro culture of biological cells for: (1) recovery of cell-secreted proteins from the culture vessel, and/or (2) other purposes, such as expansion of cells. Further, the growth media is provided to the culture vessel via a flow path that is formed using suitable tubing. Often, this tubing is present as a closed system, where the closed system includes provisions for periodic or continuous replenishment of the growth media by introduction of fresh growth media.

It is often desirable to monitor the cell culture process. Further, monitoring of the growth media in the culture vessel and/or at one or more points in the flow path is an effective way of monitoring and/or controlling the cell culture process. Typically, monitoring of the cell culture process is performed by installing sensors in the culture vessel, as well as periodically drawing a portion of the growth media or a sample having a mix of cells and the culture media from the culture vessel for analysis. Thus, for example, analysis of the growth media before, during, and after passage through the culture vessel for monitoring one or more process conditions may provide significant information regarding one or more of a number of viable cells in the culture vessel, a rate of nutrient consumption by the cells, a rate of product secretion, cell growth rates, stages of cell growth, presence or absence of subdivision of cells, and the like. Non-limiting examples of such process conditions may include nutrient components, cell-secreted proteins, cell-secreted metabolites, or the like. Such information may be used to monitor the system and/or to indicate changes that may require alteration of the process conditions, the composition of the growth media, or the like to optimize the cell culture process.

Further, it is required for the cell culture process to be carried out under aseptic conditions as in the absence of the aseptic conditions the cells may be contaminated thereby resulting in contamination of products recovered therefrom and/or loss of cell viability. As a consequence, in vitro animal cell culture systems and their component parts are initiated and maintained under sterile conditions, with each portion or the entirety of the system being sterilized prior to commencement of the process, and using sterile culture medium and uncontaminated seed cell stocks.

However, during sampling there is a need to ensure that sampling of the culture media or the sample is carried out in a manner so as to avoid introduction of contaminants into the pre-established sterile system. Conventional techniques for accomplishing this sterile withdrawal of the sample are elaborate, expensive, and time consuming. By way of example, in some of the existing systems, the area from which the sample is to be drawn, be it the culture vessel or the flow path to or from the culture vessel, is provided with a sample port such as in the form of a short segment of tubing or other appropriate structures. The system is then invaded via this sample port to withdraw a desirable quantity of the sample. Typically, sensors are deployed in and around the culture vessel to monitor the various parameters in the bioreactor. Further, a portion of inoculum, which is a mixture of the cells and the growth medium, is drawn from the culture vessel at different instances in time to monitor the cell culture process that is taking place in the culture vessel.

Each sampling instance requires drawing a portion of the sample from the culture vessel. Different tubes are attached to the ports or are passed through the ports of the culture vessel at different instances in time for different sampling instances. Any leakage or contamination in the tubing or in the connection between the culture vessel and the tubing may introduce contamination in the culture vessel. Additionally, every sampling instance is accompanied by a user attaching some sort of tubing either directly or indirectly to the culture vessel, thereby increasing the risk of contamination of the inoculum. By way of example, a plastic sampling bag or a syringe may be attached to the tubing to collect the sample that is drawn from the culture vessel. In addition to the increased risk of introduction of the contaminants due to coupling of the sampling bags/syringes to the culture vessel, there is also a likelihood of a portion of the sample being left in the tubing after the sampling instance. This residual sample may then be inadvertently carried over to the next sampling instance, thereby jeopardizing the purity of the sample obtained in the next sampling instance. Further, each sampling instance increases the likelihood of contamination of the inoculum. Hence, it is desirable to insure that sampling of the growth medium or culture fluid be carried out in a manner which avoids introduction of contaminants into the pre-established sterile system.

Consequently, in addition to the complex nature and risk of contamination associated with known sampling techniques, there also may exist an inherent limitation on the number or frequency of samplings which may be accommodated, either by reason of a limited number of sterilizable sequences to which a particular connector can be subjected to before severe degradation occurs or simply by reason of the inordinate amount of time needed to perform a sample withdrawal. These limitations may pose significant problems in situations where rapid and frequent sampling is required in order to monitor a potentially fast-changing situation. Still further, of course, elaborate and/or time-consuming sampling techniques can add significantly to the overall cost of the culture process.

BRIEF DESCRIPTION

In accordance with aspects of the present specification, a sampling assembly configured to facilitate aseptic sampling at one or more instances in time is provided. Further, the sampling assembly is configured to be coupled to a sample source. Further, the sampling assembly includes a first conduit having a first port and a second port, where the first port is configured to be coupled to the sample source. Moreover, the sampling assembly includes a plurality of sub-conduits having corresponding sub-ports, where each of the plurality of sub-conduits is operatively coupled to the first conduit at respective connector junctions. Also, each of the sub-ports is in fluidic communication with the first conduit. The sampling assembly also includes a plurality of sampling kits and one or more pumping devices. Further, each sampling kit of the plurality of sampling kits is operatively coupled to a respective sub-port of a corresponding sub-conduit. Moreover, the one or more pumping devices are operatively and aseptically coupled to the second port of the first conduit.

In accordance with another aspect of the present specification, a sampling system configured to facilitate aseptic sampling at one or more instances in time is provided. The sampling system includes a sample source configured to house a biological inoculum and a sampling assembly operatively coupled to the sample source. Further, the sampling assembly includes a first conduit having a first port and a second port, where the first port is configured to be coupled to the sample source. Moreover, the sampling assembly includes a plurality of sub-conduits having corresponding sub-ports, where each of the plurality of sub-conduits is operatively coupled to the first conduit at respective connector junctions. Also, each of the sub-ports is in fluidic communication with the first conduit. The sampling assembly also includes a plurality of sampling kits and one or more pumping devices. Further, each sampling kit of the plurality of sampling kits is operatively coupled to a respective sub-port of a corresponding sub-conduit. Moreover, the one or more pumping devices are operatively and aseptically coupled to the second port of the first conduit.

In accordance with yet another aspect of the present specification, a method for aseptically sampling at one or more instances in time is provided. The method includes providing a sample source having an outlet port and providing a sampling assembly configured to be coupled to the sample source. The sampling assembly is configured to facilitate aseptic sampling at one or more instances in time. Further, the sampling assembly includes a first conduit having a first port and a second port, where the first port is configured to be coupled to the sample source. Moreover, the sampling assembly includes a plurality of sub-conduits having corresponding sub-ports, where each of the plurality of sub-conduits is operatively coupled to the first conduit at respective connector junctions. The sampling assembly also includes a plurality of sampling kits and one or more pumping devices. Further, each sampling kit of the plurality of sampling kits is operatively coupled to a respective sub-port of a corresponding sub-conduit. Moreover, the one or more pumping devices are operatively and aseptically coupled to the second port of the first conduit. The method also includes providing fluidic communication between the sample source and the first conduit to facilitate flow of the sample out of the sample source and into at least a portion of the first conduit and at least a portion of a corresponding sub-conduit of the plurality of sub-conduits. Moreover, the method includes providing a negative pressure in a sampling kit of the plurality of sampling kits to facilitate a flow of at least the portion of the sample from the sample source and the corresponding sub-conduit into the sampling kit. Additionally, the method includes drawing the portion of the sample from the sample source and the corresponding sub-conduit into the sampling kit.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
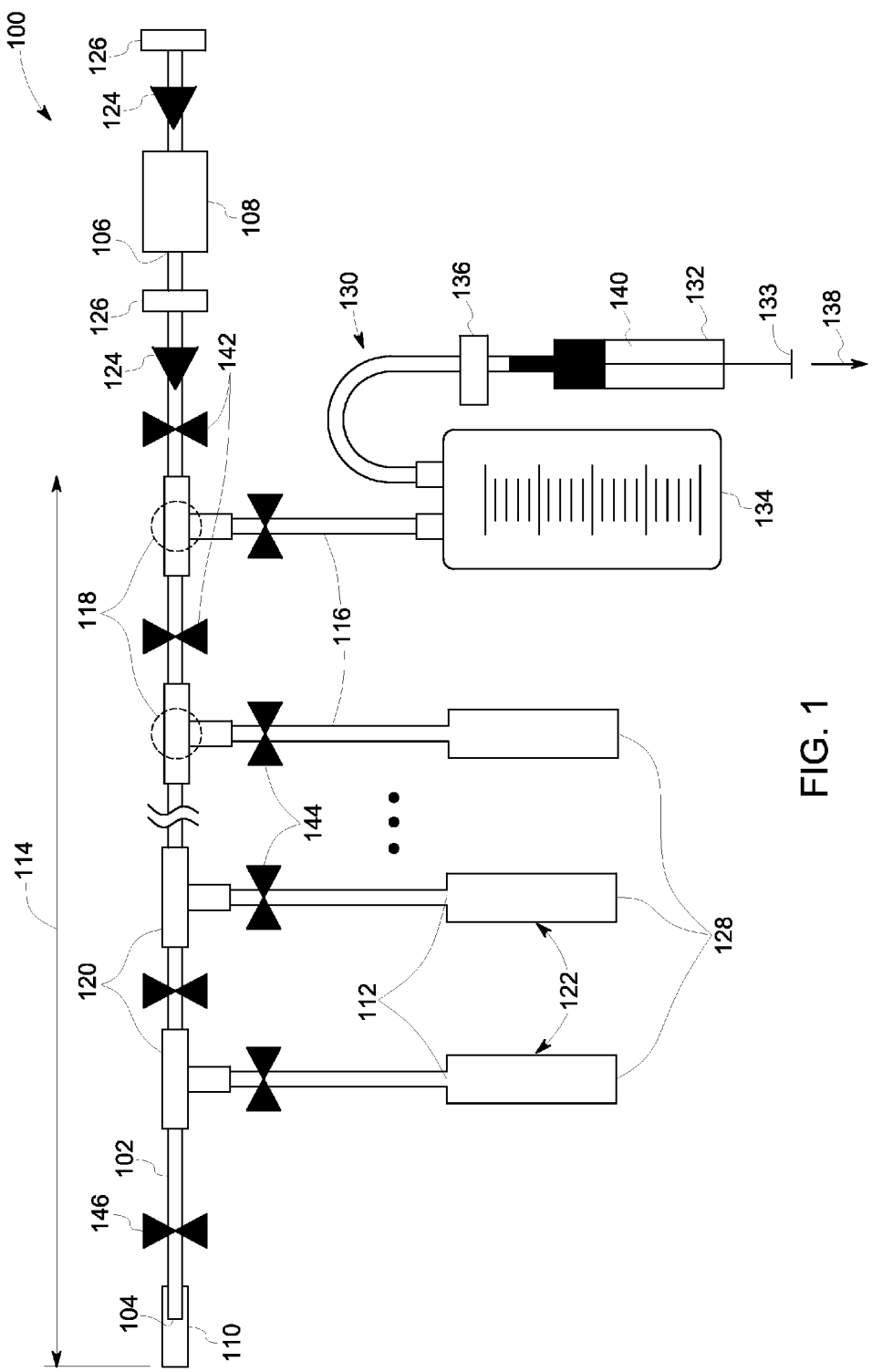
FIG. 1 is a schematic representation of a sampling assembly configured to aseptically draw one or more samples from a sample source, in accordance with aspects of the present specification.

Embodiments of the present specification relate to sampling assemblies, sampling systems and sampling methods for aseptic sampling. Further, the sampling assemblies, systems and methods facilitate aseptically drawing one or more samples from a sample source at one or more instances in time. By way of example, for in vitro culturing of biological cells, the one or more samples may be drawn for intermittent sampling and monitoring of a cell culture for recovery of cell-secreted proteins or the partial or complete removal or testing of expansion of the biological cells. Further, the sampling assemblies, systems and methods of the present specification facilitate aseptically drawing a plurality of samples at different instances in time from the same sample source while preventing sample carryover and obviating the need for separately attaching a sampling kit for each sampling instance. In particular, each sampling instance does not entail the labor intensive and time consuming step of aseptically attaching a sampling kit to the sample source.

Advantageously, the sampling assembly is configured to facilitate the plurality of aseptic sampling instances while preventing carryover of a residual sample from a previous sampling instance to the next sampling instance. The term residual sample may be used to refer to a portion of the sample that may be left in a tubing of the sampling assembly after completion of a sampling instance. In one embodiment, the sampling assemblies, systems and methods are configured to provide provisions for purging at least a portion of the sample from at least a portion of the sampling assembly after a sampling instance. In other embodiment, the sampling assemblies, systems and methods are configured to provide provisions for purging the entire tubing of the sampling assembly such that the amount of residual sample left in the tubing is zero or below detectable limits. The step of purging the portion of the sampling assembly after the sampling instance prevents carryover of the residual sample from the previous sampling instance to the next sampling instance.

In certain embodiments, a sampling assembly configured to aseptically draw samples from a sample source at different instances in time is provided. In some embodiments, the sampling assembly may not be pre-coupled to a sample source. However, in these embodiments, the sampling assembly may be configured to be coupled to different types of sample sources. Further, the sample sources are configured to house and effect production of a protein, biological sample or other cultures of interest. In one example, before using the sampling assembly for sampling, the sampling assembly may be aseptically coupled to a sample source. Moreover, the sampling assembly may be pre-sterilized before aseptically coupling the sampling assembly to the sample source. In some other embodiments, a pre-coupled sampling system having a sampling assembly aseptically coupled to the sample source may be provided.

As will be appreciated, during cell culture of cells a growth medium is used to nourish the cells. It is well known that monitoring of an inoculum at one or more instances in time is useful in monitoring and controlling the cell culture process. To that end, an inoculum including a mixture of the cells and the growth medium is monitored by intermittently withdrawing a small portion of the inoculum for analysis. Since the cell culture occurs over a period of time, sampling of the inoculum may be accomplished by drawing samples at instances separated in time. By way of example, analysis of the inoculum may be used to obtain information corresponding to number of viable cells in a culture vessel, rates of nutrient consumption by the cells and the rate of product secretion, cell growth rates, particular stages of cell growth or subdivision, and the like. It may be noted that monitoring may be performed to obtain information regarding the cell culture, and if required, to indicate a need for a change of one or more process conditions, growth medium composition, growth medium flow rate in the sample source, or the like designed to optimize the cell culture process. The cell culture process is initiated and maintained under sterile conditions, with each portion or the entirety of the system being sterilized prior to commencement of the process, and using sterile growth medium and uncontaminated seed cell stocks.

It may be noted that in case of conventional methods of sampling of the inoculum, there is a possibility of external impurities being introduced in the inoculum. Additionally, when sampling is performed at two or more instances in time, it is likely that a residual sample from a previous sampling instance is carried over to a next sampling instance. Advantageously, the sampling assemblies, systems and methods facilitate (1) aseptic sampling, and (2) minimizing or preventing carryover of the residual sample from the previous sampling instance to the next sampling instance.

Before describing the present specification in further detail, various terms used in the present specification will be defined. Use of these terms does not limit the scope of the invention but only serve to facilitate the description of the embodiments.

As used herein, the singular forms "a," "an," and "the" include plural referents unless the context clearly dictates otherwise.

As used herein the phrase, "biological samples" mean, but are not limited to, any particle(s), substance(s), extract(s), mixture(s), and/or assembly (ies) derived from or corresponding to one or more organisms, cells, and/or viruses. As will be appreciated, cells which may be cultured in an automated cell management system include one or more cell types including, but not limited to, animal cells, insect cells, mammalian cells, human cells, transgenic cells, genetically engineered cells, transformed cells, cell lines, plant cells, anchorage-dependent cells, anchorage-independent cells, and other cells capable of being cultured in vitro as known in the art. The biological sample also may include additional components to facilitate analysis, such as fluid (e.g., water), buffer, culture nutrients, salt, other reagents, dyes, etc. Accordingly, the biological sample may include one or more cells disposed in a growth medium and/or another suitable fluid medium.

Further, as used herein, the term "sample" may be used to refer to a growth medium or a mixture of cells and the growth medium.

As used herein, the term "sterile environment" refers to an environment that is substantially free of unintended microorganisms.

Moreover, as used herein, the term "sample source" refers to any suitable apparatus, such as a large fermentation chamber, bioreactor, bioreactor vessel and/or culture vessel, for growing organisms such as bacteria, cells, or yeast under controlled conditions for production of substances such as the cells, pharmaceuticals, antibodies, or vaccines, or for the bioconversion of organic waste. Further, the term "sample source" includes vessels for both aerobic and anerobic cultivation of microbial, animal, insect and plant cells, and thus encompassing a fermentor.

Further, as used herein, "cell culture" entails growth, maintenance, differentiation, transfection, or propagation of cells, tissues, or their products.

Also, as used herein the phrase "growth medium" or "growth media" means a liquid solution used to provide nutrients (e.g., vitamins, amino acids, essential nutrients, salts, and the like) and properties (e.g., similarity, buffering, and the like) to maintain living cells (or living cells in a tissue) and support their growth. Commercially available tissue growth medium is known to those skilled in the art. The phrase, "cell growth medium," as used herein, means tissue growth medium that has been incubated with cultured cells in forming a cell culture, and more preferably refers to tissue growth medium that further includes substances secreted, excreted or released by cultured cells, or other compositional and/or physical changes that occur in the medium resulting from culturing the cells in the presence of the tissue growth medium.

Additionally, as used herein, the term "sampling instance" may be used to refer to an event of drawing a sample from a sample source at a given instance in time.

Further, as used herein, the term "aseptic sampling" refers to sampling while preventing entry of contamination or external impurities in the sample source or associated components.

FIG. 1 illustrates a sampling assembly 100 configured for aseptic sampling of one or more samples from a sample source (not shown in FIG. 1). In certain embodiments, the sample source may be configured to house a biological inoculum. Further, the sample source may be a suitable culture vessel for cell expansion and growth. In some of these embodiments, the sampling may be performed to monitor a cell expansion process occurring in the sample source. Moreover, the one or more samples may be drawn from the sample source at one or more instances that are separated in time. The sampling assembly 100 includes a first conduit 102 having a first port 104 and a second port 106. In the illustrated embodiment, the first port 104 of the first conduit 102 is configured to be coupled to the sample source. Further, in operation, a portion of the biological inoculum present in the sample source may flow out of the sample source and into the first conduit 102 for a sampling instance.

In the illustrated embodiment, the second port 106 of the first conduit 102 is coupled to one or more pumping devices, generally represented by reference numeral 108. Moreover, the pumping devices 108 may be configured to provide air pressure at least in a portion of the first conduit 102 of the sampling assembly 100 to purge at least the portion of the first conduit 102 of the sampling assembly 100, for example, after a sampling instance. In certain embodiments, purging the portion of the sampling assembly 100 may include removing at least in part a residual sample from the first conduit 102, where the residual sample may be disposed in the first conduit 102 as a result of a sampling instance. In certain embodiments, the pumping devices 108 may include a mechanical pump, a motorized pump, or both. In one embodiment, non-limiting examples of the mechanical pump may include a resilient container (e.g., a resilient bulb container) with at least two flow regulators, a piston based structure (e.g., a syringe) with at least one flow regulator, or both.

It may be noted that the sampling assembly 100 may be available as a pre-sterilized and sealed arrangement. By way of example, in instances where the sampling assembly 100 is a standalone kit available to be coupled to an external sample source, the sampling assembly 100 may be pre-sterilized and sealed at the first port 104. Moreover, in some embodiments, although, the first port 104 may be initially closed for construction and sterilization of the sampling assembly 100, however, the first port 104 may be adapted to be opened to form sterile connection and liquid communication with the sample source. In one embodiment, the first port 104 of the first conduit 102 of the sampling assembly 100 may be temporarily sealed using a sealing plug 110. Further, at the time of use, the sterilized sampling assembly 100 may be coupled to the sample source by simply removing the sealing plug 110 and forming a sterile connection between the sampling assembly 100 and the sample source. In another embodiment, the first port 104 may be in the form of a closed end. At the time of use, the sampling assembly 100 may be coupled to the sample source by disengaging a portion of the first conduit 102 near the first port 104, and subsequently coupling the sampling assembly 100 to the sample source. In some embodiments, the sampling assembly 100 may be coupled to the sample source by using thermal fusion. Further, although in the illustrated embodiment, the first and second ports 104 and 106 are depicted as being situated at physical extremities of the first conduit 102 as illustrated in FIG. 1, however, alternatively, in some other embodiments, the first and second ports 104 and 106 may be disposed at locations other than the physical extremities of the first conduit 102.

Additionally, in the illustrated embodiment, the sampling assembly 100 includes a plurality of sub-ports 112 disposed along a first dimension (for example, a length) 114 of the first conduit 102. In particular, the sub-ports 112 may be disposed at respective ends of a plurality of the sub-conduits 116. Further, the plurality of sub-conduits 116 emanate from spaced-apart areas along the first dimension 114 of the first conduit 102. Moreover, the sub-conduits 116 may be coupled to the first conduit 102 at corresponding connection junctions, generally represented by reference numeral 118. The sub-conduits 116 may be selectively in fluidic connection with the first conduit 102. It may be noted that any suitable number of sub-conduits 116 may be pre-arranged along the first dimension 114 of the first conduit 102 depending upon the envisioned or desirable number of samples that may need to be drawn from the sample source during the cell culture process.

Further, the sub-conduits 116 may be coupled to the first conduit 102 using connectors 120. In one embodiment, the connectors 120 may be hollow T-shaped connectors, Y-shaped connectors, or any other suitably shaped connectors. In one embodiment, the first conduit 102 may be a continuous conduit. Further, the plurality of sub-conduits 116 may emanate from spaced-apart areas along the first dimension 114 of the first conduit 102. Alternatively, in another embodiment, the first conduit 102 may be a combination of interconnected portions of conduits. By way of example, the first conduit 102 may be formed from lengths of interconnected portions of the conduit or tubing that is connected at the connection junctions 118. In one such example embodiment, the sampling assembly 100 may be formed by one or more manifolds that are operatively coupled in fluidic communication with one another. In one embodiment, the manifolds may be made from hollow T-connectors, Y-connectors, or the like. Further, liquid-tight and aseptic sealing at the connector junctions 118 may be facilitated by arranging suitable connectors 120 and the conduit 102 and sub-conduits 116.

In certain embodiments, the sampling assembly 100 may include a plurality of sampling kits generally represented by reference numeral 122. The sampling kits 122 are aseptically coupled to the sub-conduits 116. In particular, each sampling kit 122 is coupled to a respective sub-port 112 of the plurality of sub-ports 112 of the respective sub-conduit 116. It may be noted that shape, size and number of the sampling kits 122 may vary based on sampling requirements. By way of example, the number of sampling kits 122 may be decided based on sampling instances that may be envisioned. Moreover, in some embodiments, each sampling instance may use a corresponding sampling kit 122. Accordingly, the plurality of sampling kits 122 may be used to perform the plurality of sampling instances to aseptically draw samples from the sample source. In a particular example, the number of sampling instances that may be carried out using the sampling assembly 100 may be less than or equal to the number of sampling kits 122 present in the sampling assembly 100.

Further, it may be noted that the sampling kits 122 may be sterilized before coupling the sampling kits 122 to the sub-ports 112. Moreover, since the sampling kits 122 are pre-coupled to the sub conduit 116, several steps that are associated with each sampling instance in conventional methods of sampling may be avoided. Non-limiting example of such steps that are typically performed before or during a sampling instance for conventional sampling methods include (1) disposing the sample source and any associated tubing in a sterile environment (for example, a laminar hood), (2) sterilizing a given sampling kit, (3) processing the tubing or the sample source to prepare the tubing or the sample source to receive the sampling kit, where processing may include sterilizing, and (4) aseptically coupling the sampling kit to the sample source. Advantageously, the sampling assembly 100 of the present specification and associated sampling methods of the present specification circumvent these labor intensive and time consuming steps. In particular, the sampling assembly 100 and associated aseptic sampling methods do not require steps (1) to (4) to be performed for each and every sampling instance. Hence, in addition to aseptic sampling, the sampling assembly 100 of the present specification also provides easy, time efficient sampling for a plurality of sampling instances.

In the illustrated embodiment, the second port 106 that is operatively coupled to the one or more pumping devices 108 may also be operatively coupled to one or more flow regulators 124 and/or air filters 126. In certain embodiments, the flow regulators 124 may be used to define a direction of flow of the residual sample. Also, the air filters 126 may be used to filter impurities from ambient air before pumping the filtered ambient air into at least a portion of the first conduit 102 of the sampling assembly 100. In case of piston based device, the piston based pumping devices, the sample may be exposed to the outside air present outside the sampling assembly through the piston based pumping devices. Accordingly, in instances where the outside environment is not sterile, it is desirable to use one or more air filters 126 to filter the air coming out of the piston based pumping device before introducing this air into the sampling assembly 100.

Further, the pumping devices 108 in conjunction with one or both of the flow regulators 124 and the air filters 126 are configured to facilitate purging of at least a portion of the first conduit 102 of the sampling assembly 100. Consequently, the pumping devices 108 in conjunction with one or both of the flow regulators 124 and the air filters 126 are configured to prevent carryover of the residual sample from one sampling instance to one or more successive sampling instances. In particular, the pumping devices 108 in conjunction with the flow regulators 124 are configured to purge the associated portion of the first conduit 102, while preventing the residual sample from moving towards the pumping devices 108. Accordingly, the sampling assembly 100 of the present specification is configured to facilitate maintenance of sterility of the sampling assembly 100 as well as that of the biological inoculum. In certain embodiments, following a particular sampling instance, the pumping devices 108 may be used to purge at least a portion of the first conduit 102 of the sampling assembly 100, where at least the portion of the first conduit 102 may have come in physical contact with the sample during that particular sampling instance. Further, the portion of the first conduit 102 that comes in contact with the sample may vary from one sampling instance to another.

In certain embodiments, the first conduit 102 and the plurality of sub-conduits 116 may be made of poly-vinyl chloride (PVC), polyethylene (PE), or both. However, other materials may also be employed to form the first conduit 102 and/or the sub-conduits 116. Further, the material of the conduit 102 and sub-conduits 116 may be suitable for sterilization processes. In one embodiment, the sampling assembly 100 may be pre-sterilized using sterilization methods, such as, but not limited to, gamma radiation sterilization, ethylene oxide (ETO) sterilization, hydrogen peroxide sterilization, or any other suitable sterilization methods.

In one embodiment, the sampling kits 122 may be made of plastic materials with open sampling ends suitably sized and shaped so as to be compatible with open exit ends or sub-ports 112 of the sub-conduits 116. Further, a liquid-tight and aseptic seal may be achieved between the sampling kits 122 and the sub-conduits 116 through a force-fit or mechanical bonding. Additionally, the liquid-tight and aseptic seal between the sampling kits 122 and the sub-conduits 116 may be further enhanced by applying a compressive force about respective peripheries of the sub-ports 112 of the sub-conduit 116. Alternatively, a liquid-tight and aseptic seal may be achieved between the sampling kits 122 and the sub-conduits 116 using chemical bonding or mechanical fitting, such as one or more barbs.

Non-limiting examples of the sampling kits 122 may include a resilient sampling pillow, an enclosed sampling syringe, a combinations of a rigid sampling container and a sampling syringe, or combinations thereof. It may be noted that the terms, "resilient sampling pillow" and "sampling pillow" may be used interchangeably throughout the specification. It may be noted that the sampling pillow may be a resilient structure that after being squeezed and released, is configured to regain majority of the original shape. In one example, the resilient container is configured to regain 50% to about 100% of the original shape of the sampling pillow. Further, in one example, the enclosed sampling syringe may include a syringe that is at least partly disposed in an enclosure to prevent any impurities from the surrounding environment from entering the sampling syringe. Further, in one example, a suitable flexible plastic such as nylon film may be used to form a bag-like enclosure about the sampling syringe. Moreover, the enclosure may extend to a point of connection of the sampling syringe and the respective sub-port 112 to ensure sterility inside the sampling syringe through the enclosure material when the syringe is manipulated to draw the sample.

It may be noted that the arrangement of the sampling kits 122 disposed along the length 114 of the first conduit 102 may be in any convenient configuration. By way of example, the various sampling kits 122 may or may not be disposed in an equi-distance configuration along the first conduit 102. Further, the sampling kits 122 may or may not extend in the same direction from the primary conduit 102. Although not illustrated, in an alternative embodiment, the sampling kits 122 may be alternately disposed on opposite sides along the length 114 of the first conduit 102. Further, it may be noted that some or all of the sampling kits 122 may be same or different. By way of example, in the illustrated embodiment, sampling kits 128 are different from a sampling kit 130. In the illustrated embodiment, the sampling kits 128 include containers that are resilient and are able to regain at least in part their original shape after being deformed. Once such non-limiting example of the sampling kits 128 may include resilient sampling pillows. Further, the sampling kits 128 are operatively coupled to their respective sampling ports 112.

In addition, the sampling kit 130 includes a syringe 132 that is operatively coupled to a sampling container 134 via an air filter 136. In certain embodiments, the air filter 136 may be configured to prevent any impurities from the surrounding environment from entering the sub-conduit 116 or the first conduit 102 and consequently, the sample source. By way of example, when a head 133 of the syringe 132 is drawn or pulled back in a direction represented by arrow 138, a barrel 140 of the syringe 132 is exposed to the air present in the surrounding non-sterile environment. Advantageously, introducing the air filter 136 between the syringe 132 and the rigid sampling container 134 ensures that the sampling container 134 remains sterile and the rigid sampling container 134 is not exposed to the air of the non-sterile environment. Moreover, in the illustrated embodiment, the sampling container 134 is coupled to the respective sampling port 112. In one embodiment, the sampling container 134 is a rigid plastic vessel or bottle that does not collapse substantially when the corresponding syringe 132 is pulled out to draw the sample in the sampling container 134. In one example, it may be desirable to employ the sampling kit 130 in instances where it is required to draw a larger volume of the sample into the sampling container 134.

In certain embodiments, in addition to the flow regulators 124, the sampling assembly 100 may include additional one or more flow controllers and/or flow regulators designed to facilitate sampling, assisting in purging at least a portion of the first conduit 102, corresponding sub-conduits 116, and preventing a residual sample from returning to the sample source, such as a culture vessel. Further, the sampling assembly 100 is configured to enable aseptic sampling of the culture vessel one or more times during a process, such as, but not limited to, a cell expansion process, without substantial carry over contamination from one sampling instance to the next sampling instance.

In the illustrated embodiment, each sub-conduit 116 of the plurality of sub-conduits 116 may be used for a single sampling instance. Further, subsequent to the sampling instance, the respective sub-conduit 116 may be isolated using a corresponding flow controller. In particular, the sub-conduit 116 may be isolated immediately after purging the sub-conduit 116. In some embodiments, a sealer, such as a mechanical sealer, a thermal sealer, or both may be used to seal the sub-conduit 116 at two or more locations. Subsequently, the sub-conduit 116 may be cut between the two sealed locations on the sub-conduit 116. In a non-limiting example, the sealer may include a bar sealer. It may be noted that cutting the sub-conduit 116 between the two sealed locations enables aseptically decoupling a corresponding sampling kit 122 from the sampling assembly 100. Further, cutting the sub-conduit 116 between the two sealed locations ensures that the distal end of a remaining sub-conduit 116 that is still attached to the first conduit 102 remains hermetically sealed upon separation of the sampling kit 122.

In certain embodiments, in operation, samples may be drawn through a particular sub-conduit 116 using a plurality of first flow controllers 142 and a plurality of second flow controllers 144. Additionally, one or more third flow controllers 146 may be employed, such that the third flow controllers 146 are directly coupled to the sample source. As illustrated, in certain embodiments, the flow controller 146 may be disposed between the sample source and the connector junction 118 disposed closest to the sample source. Further, the flow controller 146 may be operatively coupled to the sample source to enable flow of at least a portion of the sample from the sample source to one or more sampling kits 122. Alternatively, in some embodiments, the sampling assembly 100 may not employ the flow controller 146. In certain embodiments, one or more first flow controllers 142 may be disposed along the length 114 of the first conduit 102. In particular, the first flow controllers 142 may be disposed between neighboring connector junctions 118.

Further, the first flow controllers 142 may be configured to control flow of the sample from the sample source to the sub-conduits 116. In addition, each second flow controller 144 may be disposed between the sampling kits 122 and the first conduit 102. Specifically, one or more second flow controllers 144 may be operatively coupled to each sub-conduit 116 of the plurality of sub-conduits 116. In operation, the sample may be drawn only in a portion of the first conduit 102, where the portion of the first conduit 102 extends between the sample source and a respective sub-conduit 116 that connects the sample source to the corresponding sampling kit 122. Further, in a non-limiting example, one or more samples may be drawn at same or different instances in time using the sampling kits 122 in a sequential order starting from the sampling kit 122 disposed closest to the sample source. However, using the sampling kits 122 in the sequential order may or may not be necessary.

Among other advantages of the sampling assembly 100 of the present specification is the ease with which the sampling assembly may be constructed, used and easy availability of materials that are used in the sampling assembly, which may be easily and readily sterilized. In the device shown in FIG. 1, for example, the first conduit 102 and the sub-conduits 116 may be made of any suitable biologically inert material which is sufficiently rigid to maintain a liquid conduit bore therein and to permit interconnection using suitable connection devices, while at the same time being sufficiently flexible to permit bending and working as may be needed to effect connections.

It may be noted that although not illustrated, various other embodiments of the present specification are envisioned. By way of example, the first conduit 102 may be a T-shaped connector, where the secondary branch may have one or more sub-ports. Also, instead of a single first and second flow controller for each sub-conduit 116 and sampling kit 122, two or more first and/or second flow controllers 142 and 144 may be disposed between two sub-conduits 116, or operatively coupled to the sampling kits 122. By way of example, two first flow controllers 144 may be disposed between two sub-conduits 116 as a safety measure in the scenario where one of the first flow controllers 144 may fail to respond.

In certain embodiments, the various components of the sampling assembly 100, such as, but not limited to, the sample source, the first conduit 102, the sampling kits 122, and the like are sterilized prior to being coupled to form the sampling assembly 100. Optionally, in some embodiments, the first port 104 of the first conduit 102 which is to be arranged in liquid communication with the sample source may be closed upon initial construction. Further, the sampling assembly 100 may be sterilized by any suitable means, including irradiation since no metal parts are involved.

Advantageously, the sampling assembly 100 of the present specification is a functionally closed arrangement. In particular, the sampling assembly 100 does not permit unintended micro-organisms to enter the sampling assembly 100. By way of example, sampling kits, such as, sampling pillows, enclosed sampling syringes or sampling syringes coupled to sampling containers, include a single outlet. This single outlet is aseptically coupled to the respective sub-ports 112. Also, the sampling kits do not provide a point of entry for the unintended micro-organisms to enter the sampling assembly 100. Further, since the sampling assembly 100 is a functionally closed sampling assembly, need for employing a flow regulator between the first conduit 102 and the first port 104 of the first conduit or a sampling port of the sample source is obviated, thereby allowing at least a portion of the residual sample to be returned to the sample source. In particular, since the sampling assembly 100 is a functionally closed assembly, it is acceptable if the residual sample from the tubing of the sampling assembly 100 is returned to the sample source, as the residual sample is not likely to contain unintended micro-organisms that may otherwise be present in the tubing in case of an functionally open sampling assembly.

Figure 2:
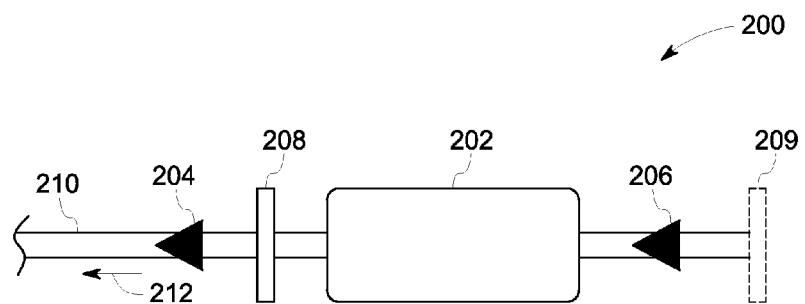
FIG. 2 is a schematic representation of an exemplary pumping device employing a resilient container configured to facilitate purging of a portion of a first conduit of the sampling assembly, in accordance with aspects of the present specification.
Figure 3:
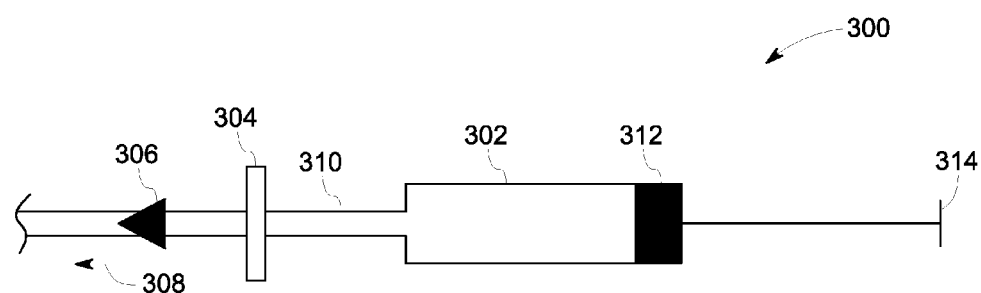
FIG. 3 is a schematic representation of an exemplary piston based pumping device, in accordance with aspects of the present specification.
Figure 4:
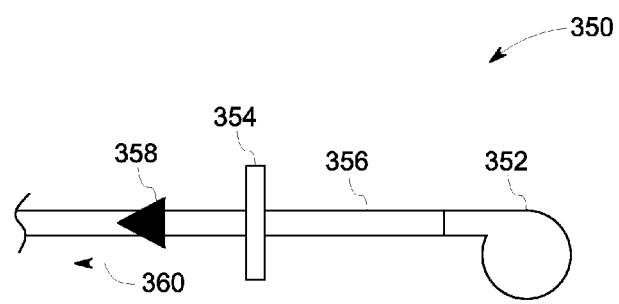
FIG. 4 is a schematic representation of an exemplary mechanical pump, in accordance with aspects of the present specification.

FIGS. 2-4 illustrate non-limiting embodiments of pumping devices for use in a sampling assembly (such as the sampling assembly 100 of FIG. 1) of the present specification. In the illustrated embodiment of FIG. 2, a schematic representation 200 illustrates a resilient container 202 configured to act as a pumping device. Further, the resilient container 202 is operatively coupled to flow regulators 204 and 206 disposed in a tubing of the resilient container. Further, the flow regulators 204 and 206 are gas flow regulators. The resilient container 202 is also coupled to an air filter 208, where the air filter 208 is configured to filter the ambient air before the ambient air enters the sampling assembly through the pumping device. In certain embodiments, the resilient container 202 may be a resilient structure that, after being squeezed and released, is able to regain majority of the original shape. In one example, the resilient container 202 is configured to regain 60% to about 100% of the original shape.

In operation, after a sampling instance, or at the beginning of a successive sampling instance, air may be pumped in the sampling assembly using the resilient container 202 to purge at least a portion of a first conduit 210 of the sampling assembly. The flow regulator 204 may be configured to prevent inadvertent flow of the sample from the first conduit 210 into the resilient container 202. Further, the flow regulator 206 may be configured to facilitate flow of the air from the resilient container 202 into the tubing in a direction depicted generally by reference numeral 212. The flow of air in the direction 212 forces a residual sample present in the first conduit into a sample source (not shown in FIG. 2).

Further, it may be noted that reference numeral 209 illustrates an alternative position of another air filter, such as the air filter 208 that may be employed in the illustrated embodiment of FIG. 2. In some embodiments, both the air filters 208 and 209 may be employed. Whereas, in some other embodiments, only one of the air filters 208 and 209 may be employed. Further, in some embodiments, the pumping devices, such as the resilient container 202 may be coupled to the sampling assembly, and subsequently, the arrangement having the sampling assembly and the resilient container 202 may be sterilized together.

FIG. 3 is a schematic representation 300 of an example of a piston based pumping device, where the piston based pumping device may be a syringe 302. The syringe 302 is operatively coupled to an air filter 304 and a flow regulator 306. Further, the syringe 302 is configured to direct air into a tubing of the sampling assembly (not shown in FIG. 3) in a direction generally represented by reference numeral 308 to purge at least a portion of a first conduit 310 of the sampling assembly. The purged residual sample present in the first conduit 310 may be forced into a sample source (not shown in FIG. 3) due to the air pressure from the syringe 302.

In operation, a piston 312 along with a syringe head 314 may be moved to pump air into the tubing. The pumped air may be filtered using the filter 304 before entering the tubing of the sampling assembly to maintain sterility of the sampling assembly. Further, although not illustrated, in some embodiments, the syringe 302 may be enclosed in an enclosure having sterile air. This sterile air may be pumped into the tubing for the purpose of purging. In this embodiment, the air filter 304 may or may not be employed.

In the illustrated embodiment of FIG. 4, a schematic representation 350 illustrates a mechanical pump 352 configured to act as a pumping device. Further, the mechanical pump 352 is operatively coupled to an air filter 354. The mechanical pump 352 and the air filter 354 are both coupled to a first conduit 356. Further, a flow regulator 358 is operatively coupled to the first conduit 356 to allow the flow of the air from the mechanical pump 352 into the first conduit 356 as well as into the remainder of the sampling assembly in a direction represented by arrow 360. The air filter 354 is configured to filter the ambient air before the ambient air enters the sampling assembly through the pumping device.

Figure 5:
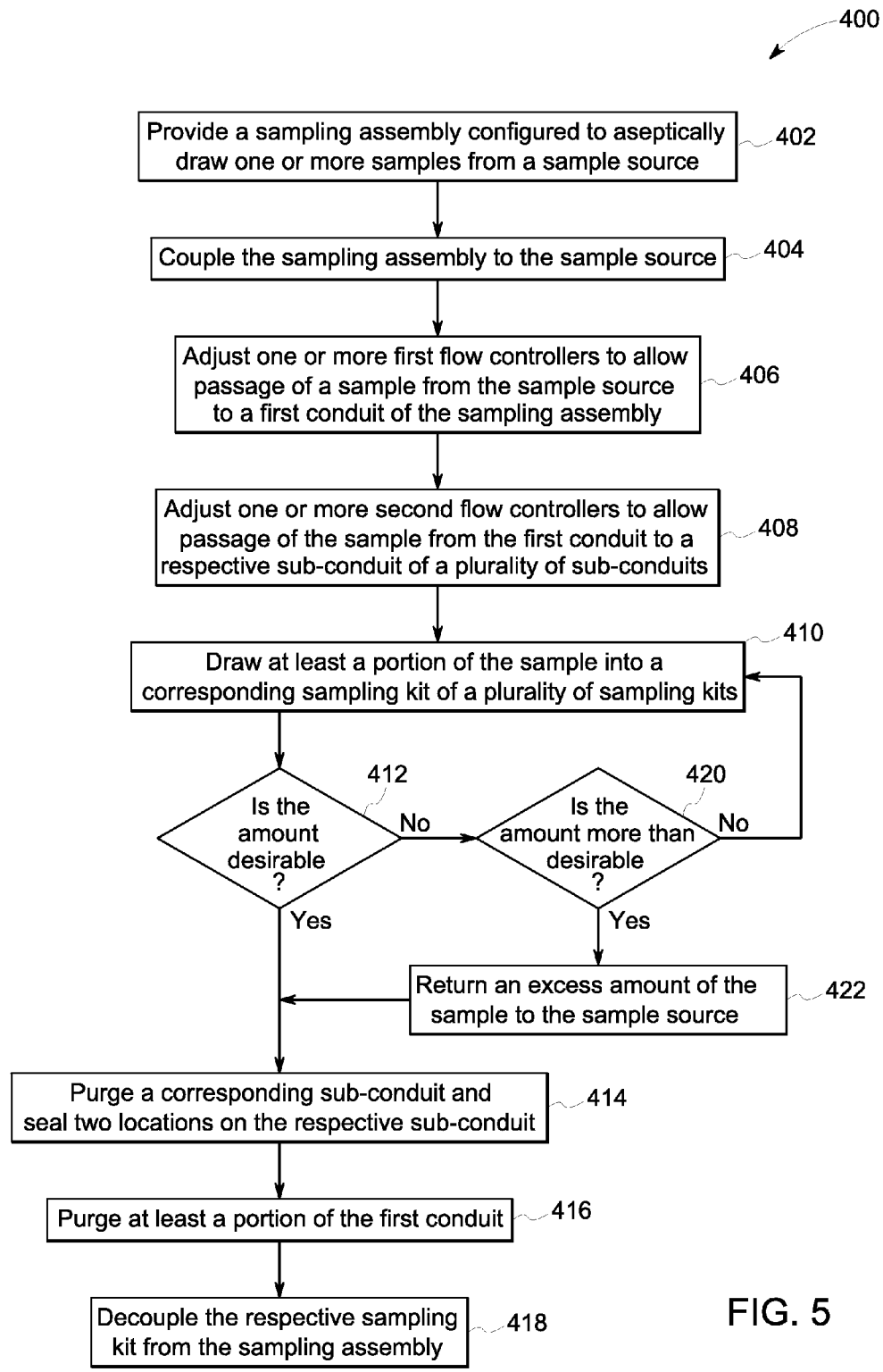
FIG. 5 is a flow chart of an exemplary method of sampling using the sampling assembly of FIG. 1, in accordance with aspects of the present specification.

FIG. 5 is an exemplary flow chart 400 depicting a method of using a sampling assembly of the present specification, such as the sampling assembly 100 of FIG. 1, to aseptically draw a sample from a sample source at one or more instances in time. In a non-limiting example, the samples may be drawn aseptically during a cell expansion process. Advantageously, the method facilitates aseptically drawing one or more samples while preventing introduction of contamination, such as unintended micro-organisms, into the sampling assembly during or after a sampling instance. Further, the method enables time efficient and aseptic sampling at one or more instances in time. By way of example, since the sampling containers and/or sampling kits are pre-coupled to a first conduit of the sampling assembly in the sterilized pre-assembled sampling assembly, a user is not required to laboriously couple a sampling kit to the sample source for each sampling instance. It should be noted that in conventional methods where the user is required to couple the sampling kit to the sample source for each sampling instance, each sampling instance of coupling the sampling kit to the sample source is accompanied by increased likelihood of introduction of contaminants into the sample source. Accordingly, the probability of introduction of contaminants into the sample source increases drastically with the increase in the number of sampling instances. Further, the sampling assembly of the present specification, by virtue of having the plurality of sampling kits that are pre-coupled to the first conduit, provides the advantage of carrying out the plurality of sampling instances in an aseptic fashion without introduction of contaminants into the sample source, which may otherwise occur in instances where a respective sampling kit needs to be individually coupled to the sample source at the time of sampling for each and every sampling instance.

In certain embodiments, a sample mixture or a biological inoculum having an inoculum of cells to be cultured may be introduced into a sample source, such as, but not limited to, a culture unit, a bioreactor, or any other suitable vessel. Further, a growth medium may be introduced in the sample source, for example to nourish the cells in the sample source. Moreover, provisions (e.g., flow controllers, flow regulators, or both) may be provided for the first conduit and/or the sampling kits such that the sampling kits and the sample source may not be undesirably influenced, e.g., during the step of drawing the sample or following the step of drawings the sample.

At step 402, a sampling assembly, such as the sampling assembly 100 of FIG. 1 configured to aseptically draw one or more samples from a sample source is provided. The sampling assembly is a pre-assembled sterilized arrangement that includes a first conduit, a plurality of sub-conduits, a plurality of sampling kits, and one or more pumping devices. Further, the first conduit includes a first port and a second port. Further, the second port of the first conduit may be coupled to one or more pumping devices. The first port may be pre-coupled to the sample source at the time of assembling of the sampling assembly. Moreover, each sub-conduit includes a corresponding sub-port. Further, one or more sub-ports are operatively coupled to a corresponding sampling kit of the plurality of sampling kits. The sampling kits may be sterilized before coupling the sampling kits to the corresponding sub-ports.

Next, at step 404, the sampling assembly may be coupled to the sample source. In particular, at the beginning of the first sampling instance of a plurality of sampling instances, the first port of the first conduit may be aseptically coupled to the sample source. Once the first port of the first conduit is coupled to the sample source, the sampling assembly may remain coupled to the sample source for the duration and number of sampling instances. Further, the step of aseptically coupling a sampling kit to the sample source may not need to be performed for each sampling instance independently. Accordingly, the sampling assembly may provide an easy to use and time efficient arrangement for the plurality of sampling instances. In one example, the first port of the first conduit may be coupled to the sample source by thermal fusion to the tube pre-attached to the culture vessel, such as a bioreactor. Alternatively, in some embodiments, the sampling assembly may be pre-coupled to the sample source to form a sampling system. The sampling system may be available as a ready to use arrangement. In these embodiments, step 404 may be redundant.

In addition, at step 406, for a sampling instance, one or more first flow controllers may be adjusted to allow passage of a sample from the sample source to the first conduit. It may be noted that for the sampling kit disposed adjacently to the sample source, if the corresponding flow controller is not disposed between the sample source and a corresponding sub-conduit, need for adjustment of the corresponding flow controller may be obviated.

At step 408, one or more second flow controllers are adjusted to allow the sample to flow from the first conduit to a respective sub-conduit of a plurality of sub-conduits of the sampling assembly. Next, at step 410, at least a portion of the sample from the respective sub-conduit is drawn into a corresponding sampling kit of the plurality of sampling kits. In one embodiment, steps 406 and 408 may be followed in same or different sequence to enable sampling. Further, for the subsequent sampling instance, one or more first flow controllers may also need to be adjusted to allow the flow of the sample from the sample source to a respective sampling kit. Further, it may be noted that in some instances, orientation of the sample source may be adjusted to allow sample to flow out of the sample source into the first conduit. In a non-limiting example where the sample is disposed in a portion of a volume of the sample source, the sample source may be tilted to allow the sample to flow to a port of the sample source that is in fluidic communication with the first conduit.

At step 412, it may be determined whether an amount of sample collected in the corresponding sampling kit is desirable. Further, it may be noted that, at step 412, if it is determined that the amount of sample collected in the sampling kit is sufficient the sample collection may be discontinued.

Moreover, at step 414, after discontinuing the collection of sample, the respective sub-conduit may be purged. In one embodiment, the respective sub-conduit may be purged using sterilized air that may be present in the corresponding sampling kit. In this embodiment, at least a portion of the sterilized air present in the corresponding sampling kit may be pumped into the corresponding sub-conduit to purge the sub-conduit. Flushing air through the sub-conduit purges the sub-conduit by removing the residual sample from the sub-conduit and allowing the residual sample to re-enter the first conduit. After purging the sub-conduit, the respective second flow controller on the sub-conduit may be immediately closed to stop any fluidic communication between the sub-conduit and the first conduit to prevent back flow of the residual sample from the first conduit into the sub-conduit. Further, after closing the second flow controller, two or more locations on the sub-conduit may be sealed. It may be noted that the two or more locations may be disposed between the flow controller and the corresponding sub-port of the sub-conduit.

Next, at step 416, an associated portion of the first conduit is purged using the one or more pumping devices. In some embodiments, the associated portion of the first conduit may refer to the portion that may have come in contact with the sample during the sampling instance. Further, one or more first flow controllers and/or flow regulators may facilitate purging of the first-conduit. In certain embodiments, for purging, the first flow controllers disposed on the first conduit between the sample source and the one or more pumping devices may be opened to establish a fluidic communication between the first and second ports of the first conduit. Specifically, the fluidic communication may be established between the first port of the first conduit and the one or more pumping devices. Next, the first conduit may be purged using the one or more pumping devices by flushing air through the portion of the first conduit disposed between the pumping device and the sample source. Flushing air through the portion of the first conduit facilitates purging of the portion of the first conduit by removing the residual sample from the first conduit and allowing the residual sample to re-enter the sample source. Advantageously, since the sampling assembly of the present specification is a functionally closed arrangement, it is acceptable to return the residual sample present to the sample source. It may be noted that in case of functionally open arrangements, it is not desirable to return the residual sample to the sample source, since the residual sample may contain unintended micro-organisms.

Accordingly, due to purging of the corresponding sub-conduit and the association portion of the first conduit, chances of a detectable amount of sample being carried over from this previous sampling instance into the next sampling instance is reduced drastically. Additionally, use of the flow regulator prevents the sample that has flown out of the sample source and into the first conduit from going back into the first conduit, thereby, retaining the sterility of the sample in the sample source. Optionally, after purging, the flow controllers disposed between the one or more pumping devices and the sample source may be closed.

It may be noted that during purging, for example, at steps 414 and 416, the sample port of the sample source may or may not be in physical contact with the biological inoculum present in the sample source.

Figure 6:
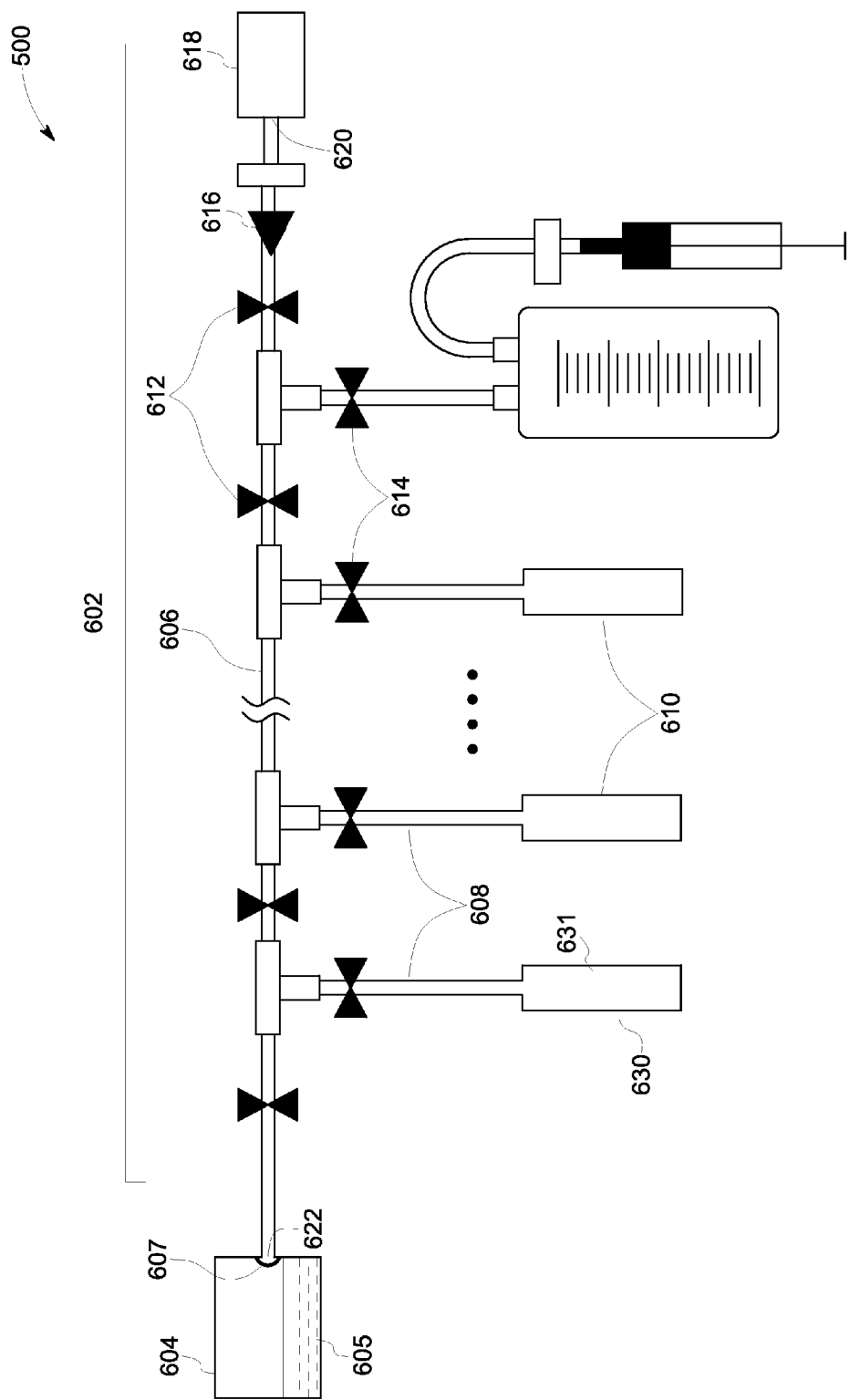
FIGS. 6-12 are schematic representations of steps involved in the method of sampling using the sampling assembly of the present specification, in accordance with aspects of the present specification.

At step 418, the corresponding sampling kit may be decoupled from the sampling assembly by disengaging a portion of the sub-conduit from the sample assembly by cutting the sub-conduit between the two sealed locations. Sealing the sub-conduit at two locations before disengaging helps in preventing introduction of any contaminants from the open end formed because of decoupling of the sampling kit. It may be noted that the steps 416 and 418 may be performed in an interchangeable sequence. In particular, the corresponding sample kit may be decoupled before or after purging the first conduit (step 416).

With returning reference to step 412, if at step 412 it is determined that the amount of the sample collected in the sampling kit is not same as the desirable amount, at step 420, a determination may be made to assess whether the amount of the sample drawn in the corresponding sampling kit is more than the desirable amount. If the amount drawn in the corresponding sampling kit is more than the desirable amount, at step 422, an excess amount of sample from the sampling kit may be returned to the sample source via the sub-conduit and the first conduit. In particular, the excess amount of sample may be returned to the sample source by compressing the sampling kit to expel the excess amount of sample from the sampling kit. Further, after expelling the excess sample from the sampling kit, steps 414 to 418 may be performed to purge the sub-conduit and the first conduit.

Moreover, at step 420, if a determination is made that the amount of sample collected in the corresponding sampling kit is less than the desirable amount of the sample, more amount of sample may be drawn and steps 410 to 418 may be performed. Further, if required, steps 420 and 422 may also be performed. Also, more sampling instances may be performed as and when desirable or until all the sub-ports, respective sub-conduits and respective sampling kits are utilized. In a particular embodiment, the sampling may be performed in a sequential order in the direction starting from the sample source and travelling towards the second port.

FIGS. 6-12 illustrate steps involved in a sampling instance using a sampling system 500 of the present specification. In one embodiment, the sampling system 500 may employ the sampling assembly 100 of FIG. 1. By way of example, FIGS. 6-12 may be considered as schematic representations of steps involved in the method of sampling of FIG. 5. FIG. 6 represents a schematic view of a sampling system 500 having a sampling assembly 602 operatively coupled to a sample source 604. Further, the sample source 604 houses a biological inoculum 605 for example, for cell expansion. In the illustrated embodiment, the sampling system 500 is available as an integrated unit having the sampling assembly 602 that is aseptically coupled to the sample source 604 to form the sampling system 500. However, embodiments where the sampling assembly 602 is available as a stand-alone ready-to-use arrangement are also envisioned within the purview of the present specification. In these embodiments, the sampling assembly 602 may be aseptically coupled to the sample source at the point of use using known techniques, such as tube fusion. It may be noted that the sampling assembly 602 or the sampling system 500 is a sterilized arrangement that is pre-fitted with sampling kits 610 and the pumping device 618.

In the illustrated embodiment, the sampling system 500 is configured to facilitate aseptic drawing of one or more samples at one or more instances in time. The sample source 604 includes a sample port or an outlet port 607. In one example, the sample source 604 may be a culture vessel, such as a bioreactor, a fermentor, or any other suitable culture vessel. In the illustrated embodiment, the sampling assembly 602 includes a first conduit 606, a plurality of sub-conduits 608 and a plurality of sampling kits 610 coupled to the first conduit 606 via the sub-conduits 608. The first conduit 606 includes a first port 622 and a second port 620. Further, the sampling assembly 602 also includes a plurality of first flow controllers 612, a plurality of second flow controllers 614, one or more third flow controllers 633, one or more flow regulators 616 and a pumping device 618.

Further, the pumping device 618 is coupled to the second port 620 of the first conduit 606. In the illustrated embodiment, the pumping device 618 may include one or more of a motorized pump, a mechanical pump (such as, resilient containers and/or syringes), or a combination of the motorized and mechanical pumps. Moreover, in instances where the sampling assembly 602 is available as a stand-alone ready-to-use arrangement, the first port 622 of the first conduit 606 may be initially hermetically sealed. In a non-limiting example, a removable seal (not shown in FIG. 6) may be used to hermetically seal the sampling assembly 602. Further, the seal at the first port 622 may be removed immediately prior to coupling the first port 622 of the sampling assembly 602 to the outlet port 607 of the sample source 604 to provide a fluidic communication between the sample source 604 and the first conduit 606.

Further, FIGS. 7-12 illustrate a sampling instance for drawing a sample into a selected sampling kit of the plurality of sampling kits 610. Moreover, as illustrated in the schematic representation 600 of FIG. 7, the selected sampling kit is a resilient sampling pillow 630. To draw the sample into the resilient sampling pillow 630, initially at least a portion of the air present in the resilient sampling pillow 630 may be expelled out of a barrel 631 of the sampling pillow 630 to generate a negative pressure in the barrel 631. In some embodiments, the resilient sampling pillow 630 may include one way port to facilitate expelling of air out of the resilient sampling pillow 630. Further, in the illustrated embodiment, the negative pressure generated in the barrel 631 of the sampling pillow 630 due to the expelled air facilitates a portion of the inoculum 605, also referred to as a sample 638 (see FIG. 7), to enter the sampling pillow 630 (see FIG. 8). In some embodiments, one or more flow controllers associated with the sampling pillow 630 may be adjusted prior to expelling the air out of the barrel 631 of the sampling pillow 630. In the particular sampling instance using the sampling pillow 630, as represented by the dashed illustrations, the third flow controller 633 and a particular second flow controller 634 of the plurality of second flow controllers 614 are adjusted to expel the air out of the barrel 631 of the sampling pillow.

Moreover, for the sample to be drawn in the sampling pillow 630, the sample 638 may be first drawn into the first conduit 606 and subsequently in the sub-conduit 636. In some embodiments, settings of the flow controllers may be retained after expelling the air from the sampling pillow 630 to allow a sample to flow into a corresponding sub-conduit of the plurality of sub-conduits 608 and subsequently in the sampling pillow 630. By way of example, the second flow controller 634 may be maintained in an open position to allow flow of the sample 638 into the sampling pillow 630 until a desirable amount of the sample is collected. Also, it may be noted that in general, initially (before starting of the sampling instance) the corresponding first flow controller 633 and the second flow controller 634 may be maintained in a closed position.

Figure 7:
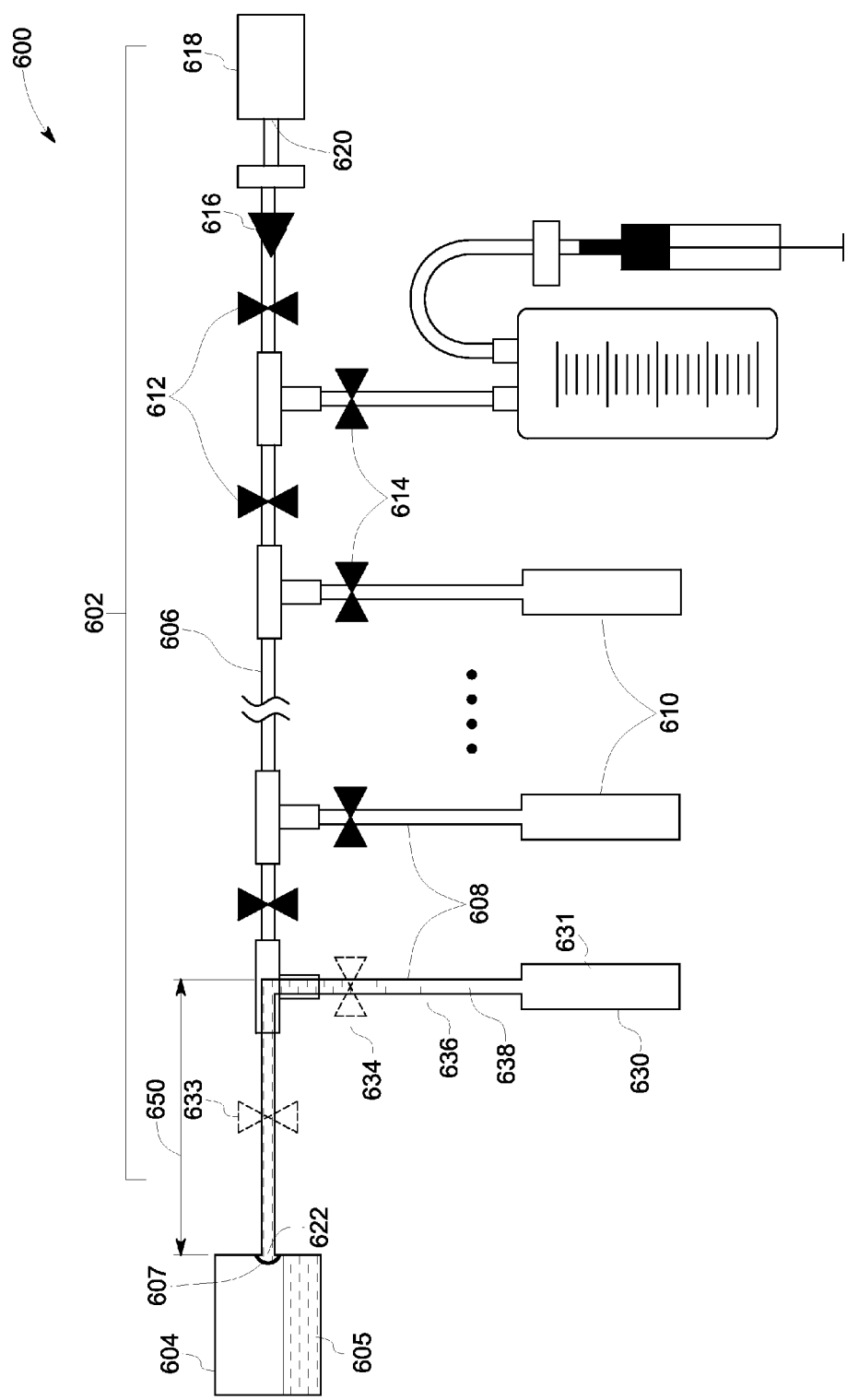
Figure 8:
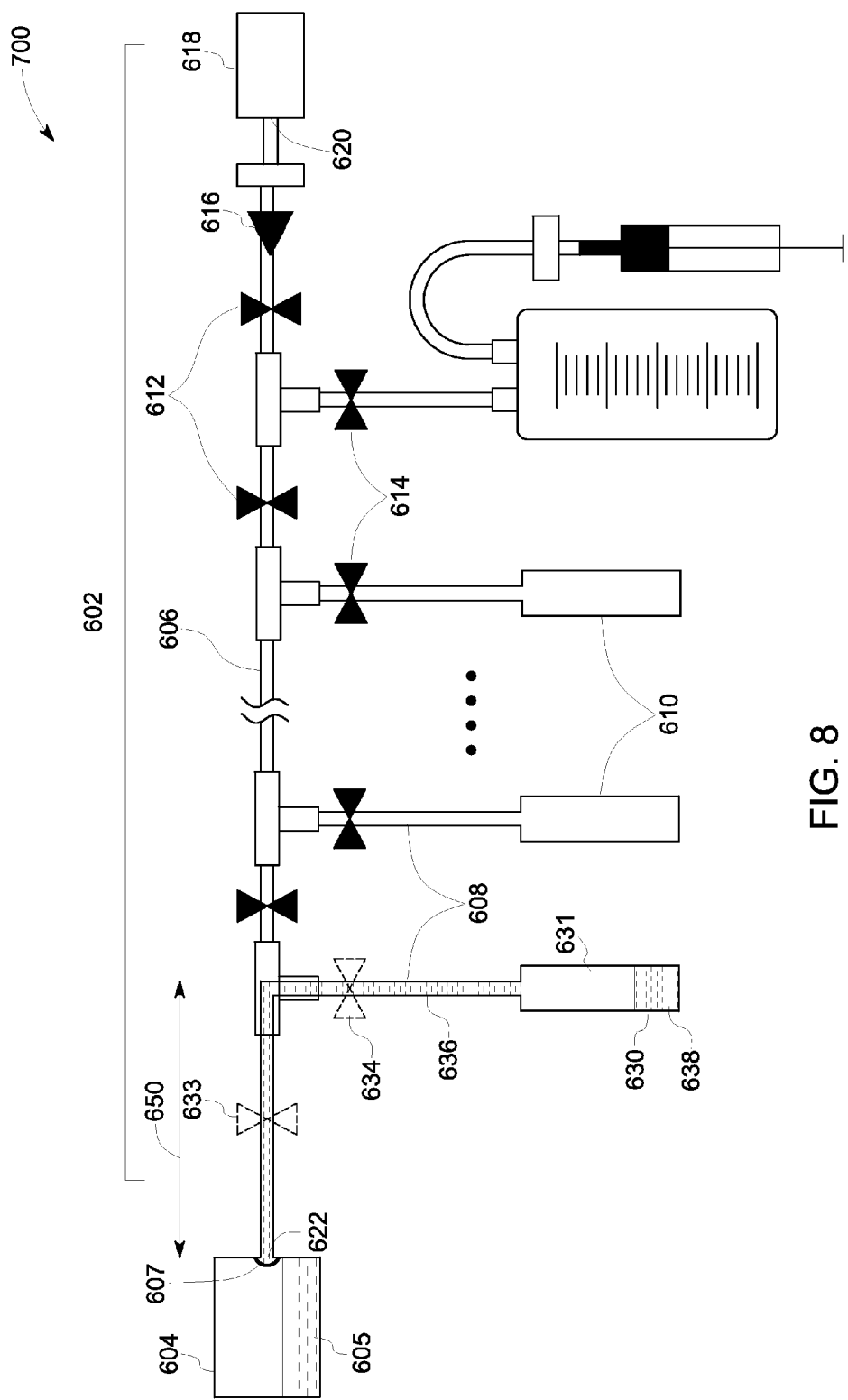

Further, as illustrated in the schematic representation 600 of FIG. 7, the sample 638 is drawn into a portion 650 of the first conduit 606 and the sub-conduit 636 by using the negative pressure that is generated at least in part in the barrel 631 of the sampling pillow 630. Further, the negative pressure may be generated in the barrel 631 while the flow controllers 633 and 634 are maintained in an open position to allow fluidic communication between the sample source 604 and the sampling pillow 630. As illustrated in the schematic view 700 of FIG. 8, the sample 638 is drawn into a portion of the barrel 631 of the sampling pillow 630.

Figure 9:
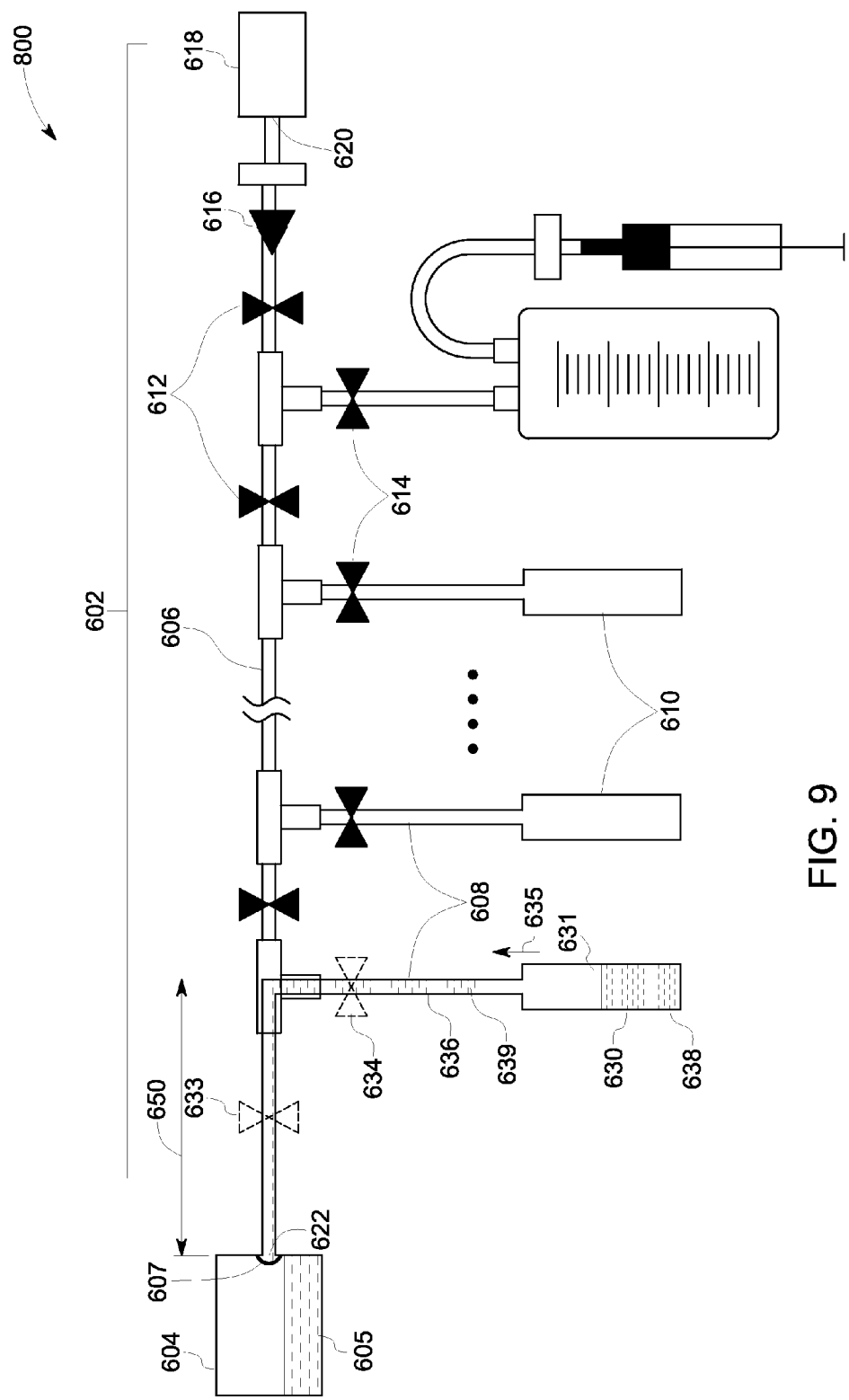

Turning now to FIG. 9, as illustrated in the schematic view 800, after the desirable amount of the sample 638 is collected in the sampling pillow 630, some amount of sample may still remain in the tubing (e.g., portion 650 of the first conduit 606 and the sub-conduit 636) between the sample source 604 and the sampling kit 610. This sample may be referred to as a residual sample 639. The residual sample 639, if not removed from the tubing, may be carried over to the next sampling instance along with the fresh sample from the sample source. Accordingly, the sampling assembly 602 is purged after each sampling instance to remove the residual sample 639 from the associated tubing pertaining to that particular sampling instance.

Further, if the desirable amount of the sample 638 is collected in the sampling pillow 630, the sampling assembly 602 is purged. The step of purging may be executed in two parts, where in the first part, the sub-conduit 636 may be purged, and in the second part, associated portions of the first conduit 606, such as the portion 650 of the first conduit 606 may be purged. For purging the sub-conduit 636, the sampling pillow 630 may be squeezed carefully to allow at least a portion of the air inside the sampling pillow 630 to exit the sampling pillow 630 as represented by arrow 635. This step of forcing the portion of the air from the sampling pillow 630 into the corresponding sub-conduit 636 facilitates purging of the sub-conduit 636 by pushing the residual sample 639 out of the sub-conduit 636.

Figure 10:
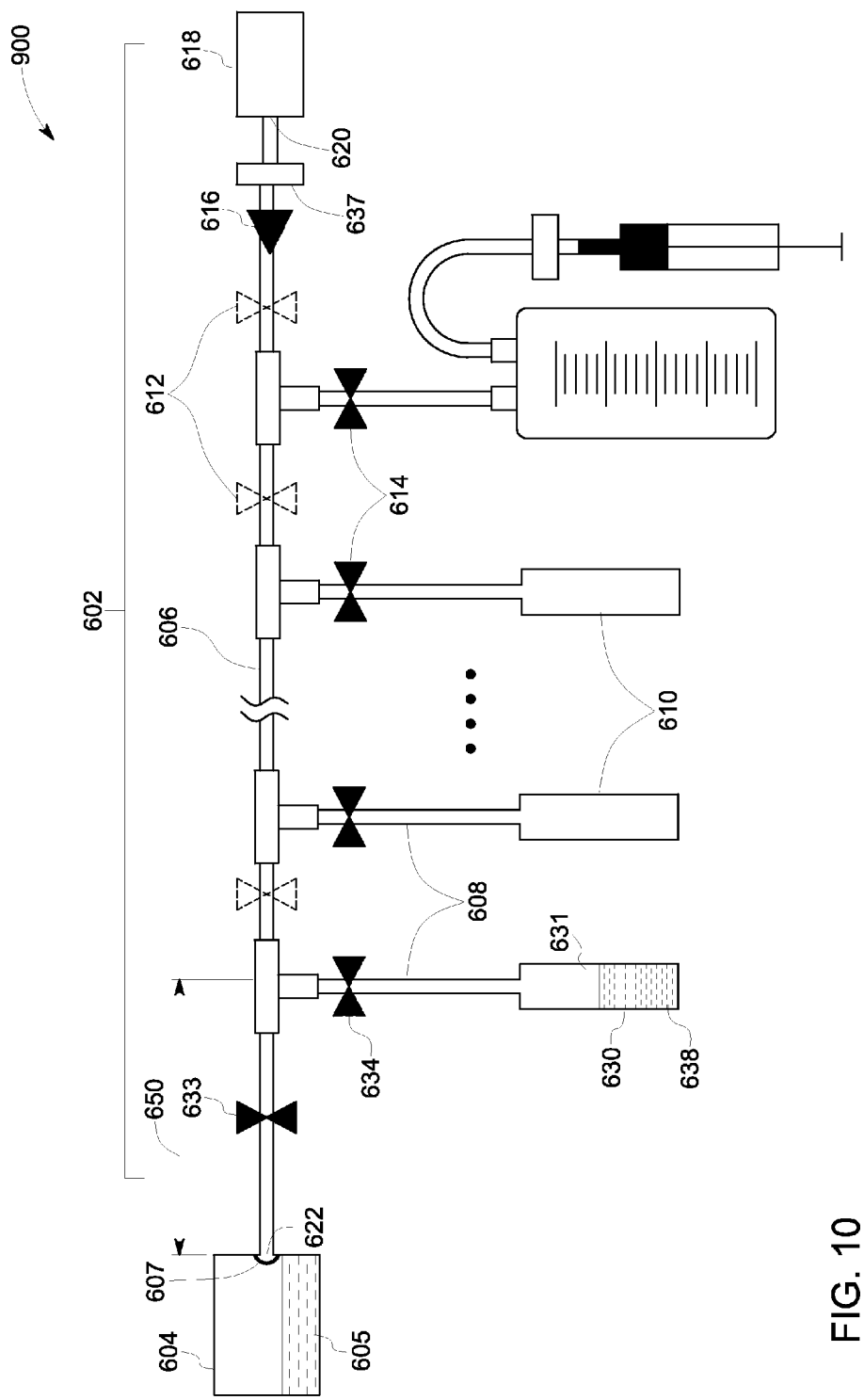

In addition, next, as illustrated in the schematic view 900 of FIG. 10, the second flow controller 634 is closed to discontinue fluidic communication between the purged sub-conduit 636 and the first conduit 606. Additionally, first flow controllers 612 disposed between the sampling pillow 630 and the pumping device 618 are set in an open position to provide fluidic communications between the first port 622 of the first conduit 606 and the pumping device 618. Subsequently, aseptic air is pumped into the first conduit 606 using the pumping device 618. In particular, aseptic air is used to return any residual sample 639 from the portion 650 of the first conduit 606 into sample source 604. The pumping device 618 may be used to flush air into the first conduit 606 one or more number of times. Use of an air filter 637 in conjunction with the pumping device 618 aids in providing aseptic air to the sampling assembly 602 for purging. Further, use of the flow regulator 616 ensures that the residual sample 639 does not accidentally enter the pumping device 618.

Figure 11:
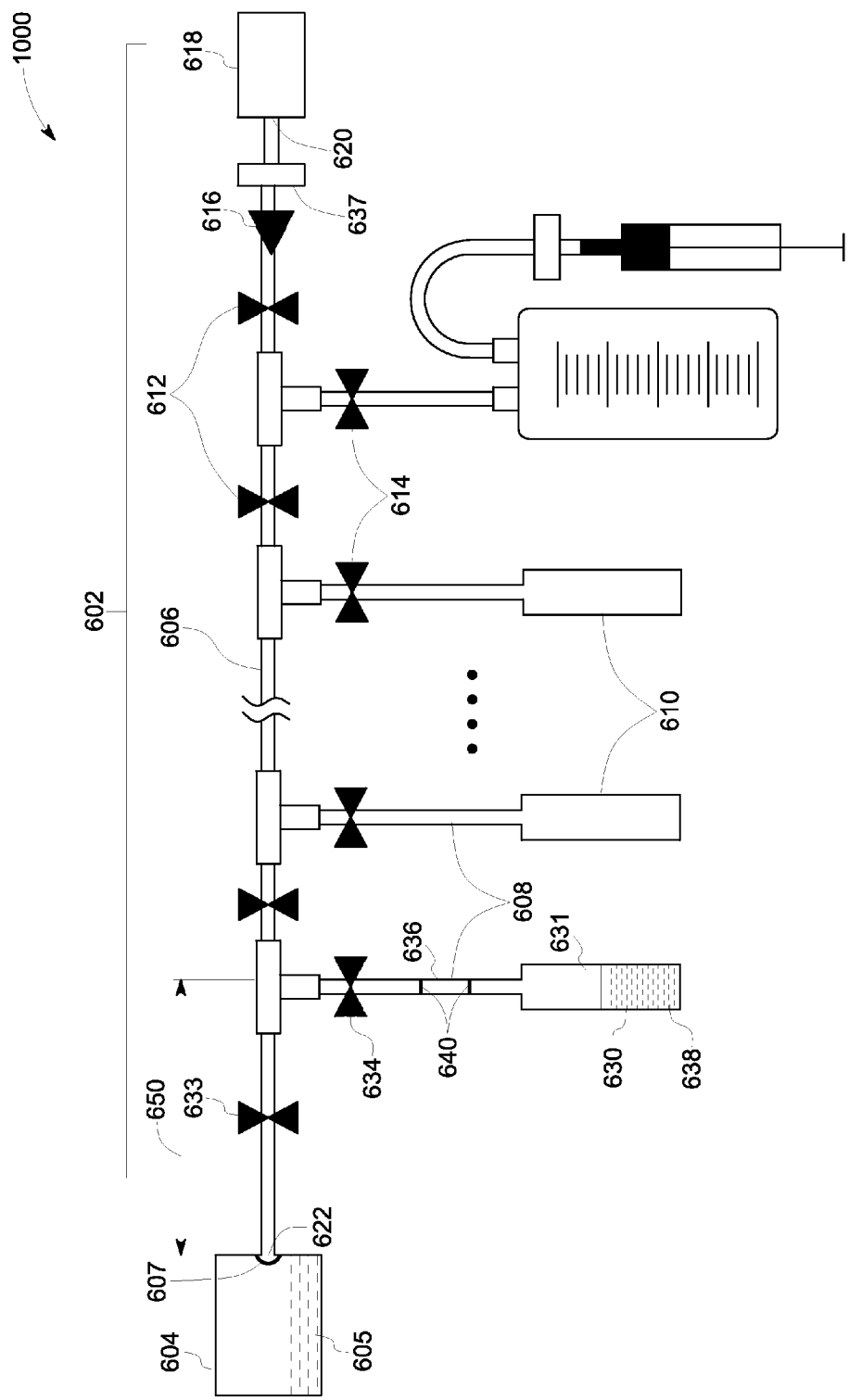

Moreover, as illustrated in a schematic representation 1000 of FIG. 11, after purging of the sub-conduit, the sub-conduit 636 is sealed at two or more locations 640. In a non-limiting example, the sub-conduit 636 may be sealed at the two locations 640 using bar sealers. Further, after purging of the first conduit 606, the first flow controllers 612 may be returned to closed positions.

Figure 12:
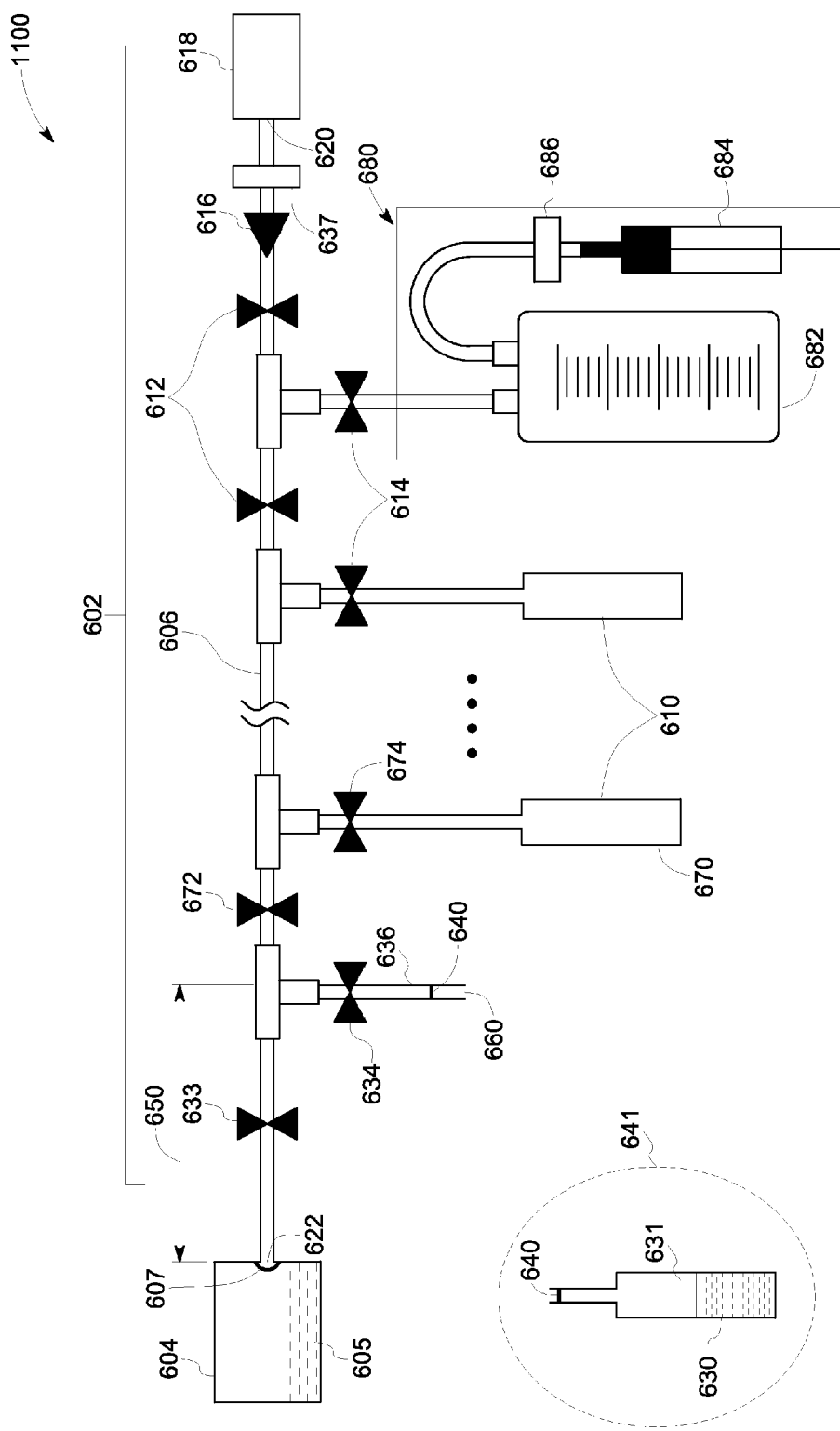

Referring now to FIG. 12, as illustrated in the schematic representation 1100, the sampling instance for the sampling pillow 630 is concluded by decoupling the sampling pillow 630 from the sampling assembly 602 by cutting the sub-conduit 636 at a location 660 disposed between the locations 640. With the locations 640 being sealed, the sampling pillow 630 as well as the sub-assembly 602 are hermetically sealed when the sub-conduit is cut at the location 660. Reference numeral 641 represents the sampling pillow 630 after the sampling pillow 630 is decoupled from the sampling assembly 602.

It may be noted that in case of a subsequent sampling instance, where a sampling kit 670 is used to draw a sample, the third flow controller 633, a first flow controller 672 of the plurality of first flow controllers 612 and a second flow controller 674 of the plurality of second flow controllers 614 may be adjusted to allow a flow of the sample from the sample source 604 towards the sampling kit 670. Additionally, it may be noted that when a larger amount of sample is desirable, a sampling kit 680 may be used to draw the sample. In the illustrated embodiment, the sampling kit 680 includes a sampling container 682, a syringe 684 and an air filter 686. The air filter 686 is disposed between the sampling container 682 and the syringe 684, so as to prevent contaminants from the surrounding environment from entering into the sampling container 682. Further, the sampling container 682 may be used when a greater volume of sample is desirable.

Advantageously, the assemblies, systems and methods of the present specification enable effective withdrawal of a sample from a sterile sample source in an aseptic, rapid and cost-effective manner. Further, since the sampling assembly is pre-assembled and sterilized, the sampling assembly and the sampling process of the present specification permit a plurality of sampling instances whereby the sterile environment is safeguarded. Further, since the sampling assembly of the present specification is a functionally closed arrangement, the residual sample or excess amount of sample from the sampling kit may be returned to the sample source without the risk of introducing unintended micro-organisms in the sample source.

While only certain features of the disclosure have been illustrated and described herein, many modifications and changes will occur to those skilled in the art. It is, therefore, to be understood that the appended claims are intended to cover all such modifications and changes as fall within the true spirit of the disclosure.

The invention claimed is:

1. A sampling assembly configured to be coupled to a sample source and facilitate aseptic sampling at one or more instances in time, comprising:
   a first conduit comprising a first port and a second port, wherein the first port is directly coupled to the sample source;
   a plurality of sub-conduits having corresponding sub-ports, wherein each of the plurality of sub-conduits is operatively coupled to the first conduit at respective connector junctions, wherein the sub-ports are disposed between the first and second ports of the first conduit, and wherein each of the sub-ports is in fluidic communication with the first conduit;
   a plurality of sampling kits, wherein each sampling kit of the plurality of sampling kits is operatively coupled to a respective sub-port of a corresponding sub-conduit; and
   one or more pumping devices directly and aseptically coupled to the second port of the first conduit.

2. The sampling assembly of claim 1, wherein the one or more pumping devices comprise a pump, a syringe, a resilient container, or combinations thereof.

3. The sampling assembly of claim 1, further comprising an air filter operatively coupled to the one or more pumping devices.

4. The sampling assembly of claim 1, further comprising at least one flow regulator operatively coupled to the one or more pumping devices.

5. The sampling assembly of claim 1, wherein the first conduit is a continuous conduit.

6. The sampling assembly of claim 1, wherein one or more sampling kits of the plurality of sampling kits comprise a resilient sampling pillow, a sampling syringe, a sampling container, or combinations thereof.

7. The sampling assembly of claim 1, further comprising a plurality of first flow controllers disposed along the first conduit.

8. The sampling assembly of claim 1, further comprising a plurality of second flow controllers operatively coupled to one or more sampling kits of the plurality of sampling kits.

9. A sampling system configured to facilitate aseptic sampling at one or more instances in time, the sampling system comprising:
   a sample source configured to house a biological inoculum;
   a sampling assembly, comprising:
      a first conduit comprising a first port and a second port, wherein the first port is directly coupled to the sample source;
      a plurality of sub-conduits having corresponding sub-ports, wherein each of the plurality of sub-conduits is operatively coupled to the first conduit at respective connector junctions, wherein the sub-ports are disposed between the first and second ports of the first conduit, and wherein each of the sub-ports is in fluidic communication with the first conduit;
      a plurality of sampling kits, wherein each sampling kit of the plurality of sampling kits is operatively coupled to a respective sub-port of a corresponding sub-conduit; and
      one or more pumping devices directly and aseptically coupled to the second port of the first conduit,
   wherein the sampling assembly comprises a functionally closed arrangement.

10. The sampling system of claim 9, further comprising a flow regulator operatively coupled to the one or more pumping devices.

11. The sampling system of claim 9, further comprising an air filter operatively coupled to the one or more pumping devices.

12. The sampling system of claim 9, wherein the plurality of sampling kits comprises a resilient sampling pillow, an enclosed sampling syringe, a combination of a rigid sampling container and a sampling syringe, or combinations thereof.

13. The sampling system of claim 12, wherein the combination of the rigid sampling container and the sampling syringe further comprises an air filter disposed between the rigid sampling container and the sampling syringe.

14. A method for aseptically sampling at one or more instances in time, comprising:
- providing a sample source having an outlet port;
- providing a sampling assembly configured to be coupled to the sample source and facilitate aseptic sampling at one or more instances in time, wherein the sampling assembly comprises:
  - a first conduit comprising a first port and a second port, wherein the first port is directly coupled to the sample source;
  - a plurality of sub-conduits having corresponding sub-ports, wherein each of the plurality of sub-conduits is operatively coupled to the first conduit at respective connector junctions, wherein the sub-ports are disposed between the first and second ports of the first conduit, and wherein each of the sub-ports is in fluidic communication with the first conduit;
  - a plurality of sampling kits, wherein each sampling kit of the plurality of sampling kits is operatively coupled to a respective sub-port of a corresponding sub-conduit;
  - one or more pumping devices directly and aseptically coupled to the second port of the first conduit;
- coupling the first port of the first conduit to the outlet port of the sample source;
- providing fluidic communication between the sample source and the first conduit to facilitate flow of the sample out of the sample source and into at least a portion of the first conduit and at least a portion of a corresponding sub-conduit of the plurality of sub-conduits;
- providing a negative pressure in a sampling kit of the plurality of sampling kits to facilitate a flow of at least the portion of the sample from the sample source and the corresponding sub-conduit into the sampling kit; and
- drawing the portion of the sample from the sample source and the corresponding sub-conduit into the sampling kit.

15. The method of claim 14, further comprising adjusting an orientation of the sample source to establish a fluidic connection between the sample source and the first conduit.

16. The method of claim 14, further comprising:
- determining if a desirable amount of sample is drawn into the sampling kit; and
- if the desirable amount of sample is drawn into the sampling kit, purging at least a portion of the corresponding sub-conduit using the sampling kit by pushing a residual sample from the portion of the sub-conduit towards the first conduit.

17. The method of claim 16, further comprising purging at least the portion of the first conduit using the one or more pumping devices.

18. The method of claim 14, further comprising sealing two or more locations on the corresponding sub-conduit of the plurality of sub-conduits.

19. The method of claim 14, further comprising decoupling the sampling kit from the sampling assembly by decoupling the corresponding sub-conduit at a location disposed between the two or more locations.

* * * * *